(12) United States Patent
Koch

(10) Patent No.: US 8,746,294 B2
(45) Date of Patent: Jun. 10, 2014

(54) METERING DEVICE FOR POWDERY SUBSTANCES

(75) Inventor: Timo Koch, Gaissau (AT)

(73) Assignee: Amann Girrbach AG, Koblach (AT)

( * ) Notice: Subject to any disclaimer, the term of this patent is extended or adjusted under 35 U.S.C. 154(b) by 812 days.

(21) Appl. No.: 13/054,950

(22) PCT Filed: Mar. 17, 2009

(86) PCT No.: PCT/AT2009/000113
§ 371 (c)(1),
(2), (4) Date: Jan. 20, 2011

(87) PCT Pub. No.: WO2010/009483
PCT Pub. Date: Jan. 28, 2010

(65) Prior Publication Data
US 2011/0121025 A1    May 26, 2011

(30) Foreign Application Priority Data
Jul. 22, 2008 (DE) .......................... 10 2008 034 130

(51) Int. Cl.
*B65B 1/20* (2006.01)
(52) U.S. Cl.
USPC ............... 141/72; 141/83; 222/181; 222/200; 366/154.2
(58) Field of Classification Search
USPC ................ 141/83, 72; 222/71, 161, 199, 200; 366/151.1, 154.1, 154.2
See application file for complete search history.

(56) References Cited

U.S. PATENT DOCUMENTS

| 1,779,850 A | 10/1930 | Maurer |
| 6,116,471 A | 9/2000 | Miller |
| 6,854,493 B2 * | 2/2005 | Ichikawa et al. ............... 141/301 |

FOREIGN PATENT DOCUMENTS

| AT | 281685 | 5/1970 |
| DE | 1556175 | 2/1970 |
| DE | 2315468 | 6/1974 |
| DE | 7427747 | 7/1975 |
| DE | 2504832 | 8/1975 |
| DE | 2510809 | 9/1976 |
| EP | 0406164 | 1/1991 |
| EP | 0459475 | 12/1991 |
| WO | 2008031232 | 3/2008 |

* cited by examiner

*Primary Examiner* — Jason K Niesz
(74) *Attorney, Agent, or Firm* — Volpe and Koenig, P.C.

(57) ABSTRACT

A metering device for powdery substances, particularly for preparing dental and dental laboratory powder compounds. The powder compounds can be filled into a storage container (1) and fed from the storage container (1) to a vessel (9) using a discharge device. The lower region (3) of the storage container (1) is tapered, and in the storage container (1) an insert (4) is arranged, which has at least one upwardly tapering section (5), wherein the insert (4) is arranged in the tapered lower region (3) of the storage container (1). A through-passage (7) remains clear between the lower edge (6) of the tapering section (5) of the insert (4) and the tapered lower region (3) of the storage container (1). The insert (4) and/or the storage container (1) is associated with a vibration unit (8). The vessel (9) receiving the metered powder can be placed on a weighing unit (10), wherein the weighing unit (10) and the vibration unit (8) are operatively connected to each other.

19 Claims, 2 Drawing Sheets

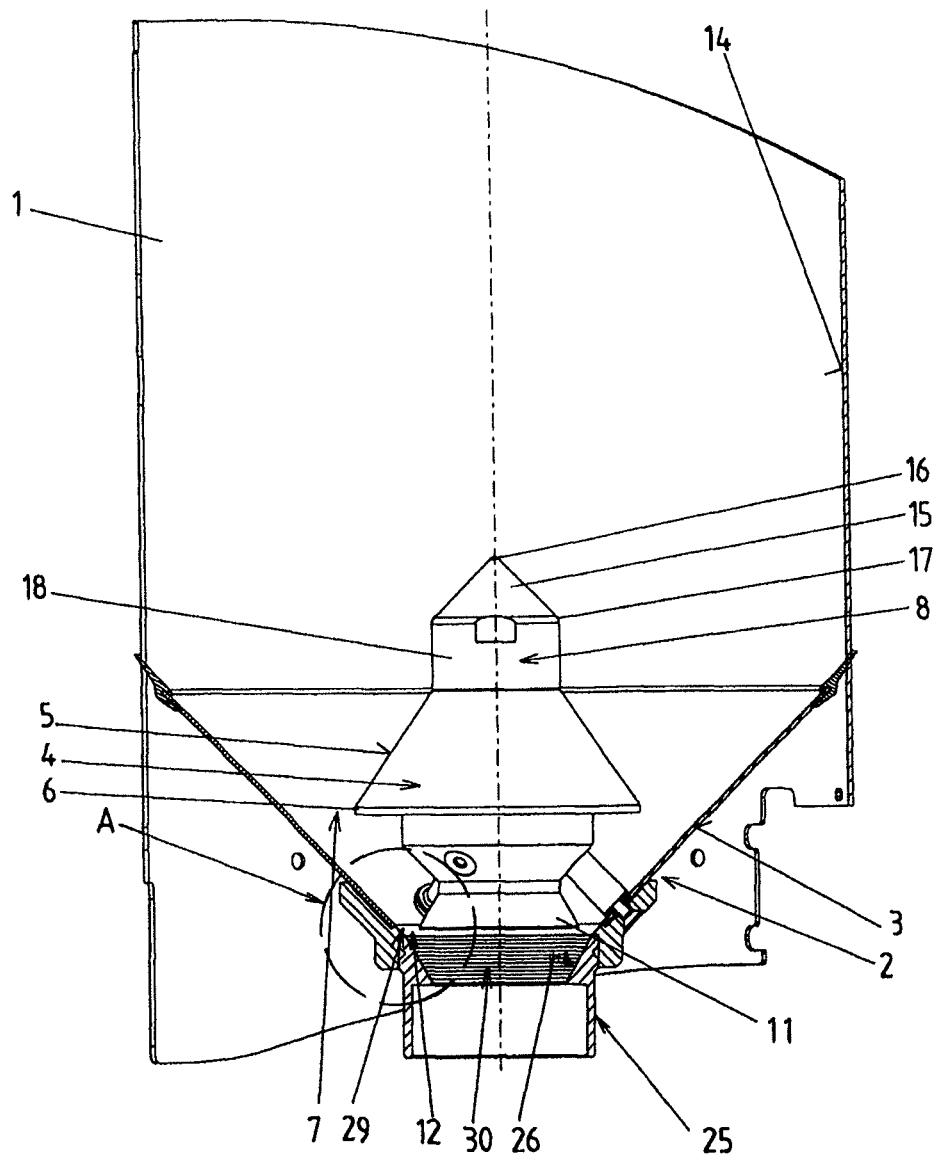
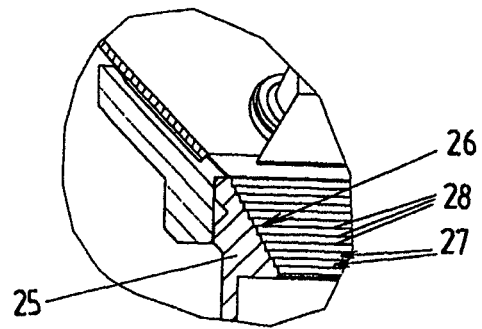

METERING DEVICE FOR POWDERY SUBSTANCES

BACKGROUND

The invention relates to a metering device for powdery substances, in particular, for the preparation of dental and dentistry-related powder compounds, wherein the powder compounds can be filled into a storage container and a discharge device is allocated to this storage container. The invention further relates to a method for the operation of a metering device.

For a known metering device for mixing one or more powdery and/or fluid substances for dentistry-related applications, the powdery substances and also the fluid substances are provided in container-like arrangements, with separate metering devices being provided for each powdery substance. For supplying and metering the powdery substances, feed screws are installed. So that the powdery substances are always fed properly to the feed screws, steep slope angles are required in the storage containers and a special sliding coating is also provided.

Devices for the dosed discharge of bulk material from a container have also already become known (e.g., DE 25 048 32A or EP 0 459 475 B1) in which, for large discharge quantities and correspondingly large storage containers, inserts that are height adjustable or that change the through-flow cross section are provided on the bottom side of a storage container, wherein vibrating units are also used. Such large installations are mechanically complicated and therefore not suitable for small metering devices, as is the case for the metering of dental powder compounds.

SUMMARY

The present invention is therefore presented with the objective of creating a metering device of the type noted above that allows metering of powdery substances and very small weight quantities and nevertheless can have a structurally simple design.

According to the invention, this is possible in that the lower region of the storage container has a tapered construction and an insert is arranged in the storage container, with this insert having at least one section that tapers upward and is arranged in the tapered, lower region of the storage container, wherein one or more passage opening(s) remains or remain free between the lower edge of the tapering section of the insert and the tapered, lower region of the storage container, and a vibration device is allocated to the insert and/or the storage container.

Through these measures according to the invention, exact metering is made possible also while maintaining very small weights. Just through the structural design and the vibration device, the exact metering is achieved without activating mechanical, electrical, or pneumatic elements for opening or closing an outflow opening. In this way, rotating and closable parts that tend to become clogged are also not required. Thus, in this sense, it is favorably provided that the storage container has a permanently open outlet opening through which powdery substance can be discharged. Through the configuration according to the invention of the lower region with a tapered construction and the insert, powdery substances can be discharged from the outlet opening only when the vibration device is turned on.

For the sake of completeness, it is noted that that the terms upper and lower relate to the operating position of the metering device. In this operating position, the outlet opening of the storage container is typically arranged underneath, that is, at a lower level than the insert and the tapering, lower region of the storage container. The outlet opening favorably forms the lower end of the storage container. The lower region of the storage container favorably has a construction that tapers downward, that is, in particular, in the direction toward the outlet opening.

Furthermore, it is preferably proposed that a vessel holding the dosed powder can be set on a weighing device, wherein the weighing device and the vibration device are in active connection with each other. In this context, the active connection is to be understood, as explained in detail farther below, as a control line or the like by which the vibration device can be controlled by the weighing device. In order to not disturb the weighing process by the vibration of the vibration device, however, the weighing device and vibration device are preferably mechanically decoupled from each other or decoupled with respect to oscillations. Through these measures, the weighing device that does indeed contain the control elements is not subjected to vibrations, so that a fine-tuning of the required powder quantity is possible.

In one special construction with simple production possibilities, it is provided that the lower region of the storage container has a construction tapered in the shape of a cone or pyramid and advantageously the insert has a conical or pyramidal section that tapers upward. Conical or pyramidal or also frustum-shaped or truncated-pyramid-shaped sections can be produced in especially simple ways.

For the construction of the metering device, it is advantageous when the passage opening has a ring-shaped, advantageously closed-periphery construction. Therefore, it is not at all required that the sections facing each other in the tapering region of the storage container and the insert touch each other.

In the scope of the invention, however, it is also conceivable that several bores or through holes or sieve-like sections are provided as passage openings. Therefore, according to the type of powder mass to be dosed, special measures can be taken.

It is further proposed that a pin or a sleeve that reduces the through-flow cross section projects downward on the bottom side of the insert. Thus a second region narrowing the through flow of the powder located in the storage container is provided, so that closure elements are not required. Nevertheless, if desired, additional closure elements could be provided.

In this context, it is especially advantageous when the passage opening(s) remaining between the tapered, lower region of the storage container and the lower edge of the tapering section of the insert is (are) larger in cross section than the ring-shaped passage opening remaining between the tapered, lower region of the storage container and the pin or the sleeve. Consequently, a passage opening that is smaller in cross section follows a passage opening that is larger in cross section, so that after turning off the vibration device, powder can no longer be discharged downward. The sections of the storage container and of the vibration insert adapted to each other thus form sufficient support against powder being discharged in an uncontrolled manner.

Even for the preliminary setting for different consistencies of various powder compounds, it is advantageous when the pin or the sleeve projecting from the bottom side of the insert is held so that it can be replaced. In this way, a rough setting for various powder compounds can be performed in advance.

Because no height adjustment or also rotation of parts of the vibration insert is required, it is advantageous when the insert is supported so that it is fixed in position relative to the tapered, lower region of the storage container. Thus, a secure arrangement of the insert is guaranteed despite the given, continuous vibrations during the discharge of the powder compounds.

In this context, it is also possible that the insert is connected rigidly to the storage container and the vibration device is arranged in the insert. In this way, the storage container can vibrate with a vibration device within the insert.

In the scope of the invention it is conceivable that a refill inspection arrangement that can be detected optically and/or acoustically is arranged on a cover or a wall of the storage container. In this way a warning that the storage container should be refilled is given in a timely manner.

One advantageous configuration provides that the insert has a conical or pyramidal section lying above the tapering section, wherein the tip of this section points upward and its lower edge has a smaller diameter than the lower edge of the tapering section and is connected to the tapering section by a cylindrical transition section. Therefore, a structurally effective measure can be created, in order to hold and optionally replace the vibration device.

A good arrangement in terms of handling is then given when the storage container is held so that it can be removed and locked together with the insert on a base frame. Thus, the storage container can be removed from the base frame for filling or for refilling and can be supported by larger containers if this should be necessary.

In this context it is advantageous when the storage container can be suspended by a hook-like, upper closure on a support pin on the base frame and is held with locking elements arranged on the lower end region so that it can be locked in the suspended position. In this way, the container is held securely and also the storage container also cannot be lifted inadvertently or by an impact.

For such a structural shape, equivalent, additional measures could also be created; then there is the possibility that in the region of the locking elements between the storage container and base frame there are plug devices for the electrical connection for operation of the vibration device. Therefore, when the storage container is removed, the electrical connections are also equally separated and the connection is re-established when they are inserted or suspended again.

So that the transmission of vibrations to the base frame is stopped, it can be provided that advantageously strip-like intermediate layers made from a vibration-blocking material are arranged between the storage container and base frame.

One especially simple construction and thus also assembly or disassembly of the storage container is then given when the essentially cylindrical storage container and the tapered lower region are formed from two sections separated from each other, wherein a sealing element closed on the periphery is arranged on the upper peripheral edge of the tapered region.

In the scope of the invention it is also conceivable that the vibration frequency can be set or preset in steps or continuously for adapting to different types of powder compounds. In this way, various consistencies of powder compounds to be dosed can also be taken into account.

One method for operating a metering device provides that the vibration device is operated at the beginning and at the end of the metering process with a smaller vibration frequency than in an intermediate phase of the metering process. In this way it is achieved that the powder compounds are prepared for a metering, that is, are moved slowly in the metering direction. Then the metering of the main quantity of the powder compounds is performed. At the end of the powder process, in practice the metering process is then reduced again so that an exact, desired metering quantity is produced.

In this context it is advantageous when the weighing device sets the control of the vibration period after a special processing step. Then, depending on the required quantity, the beginning and the ending phase of the metering are also produced.

Another possibility of the method provides that the vibration device is completely turned off in a way that can be preset before reaching the desired feed quantity and then, for the fine metering, the vibration device is switched to a maximum value of the vibration frequency and the vibration frequency is reduced from this setting continuously or in steps to a minimal value, advantageously zero. In this way a good adjustment to the exact fine metering can be achieved at the end of the metering.

BRIEF DESCRIPTION OF THE DRAWINGS

Additional features according to the invention and special advantages are explained in more detail in the following description with reference to the drawing.

FIG. 2 shows, in a cutout, a second embodiment according to the invention.

FIG. 3 shows the detail A from FIG. 2 enlarged.

DETAILED DESCRIPTION OF THE PREFERRED EMBODIMENTS

Figure 1:
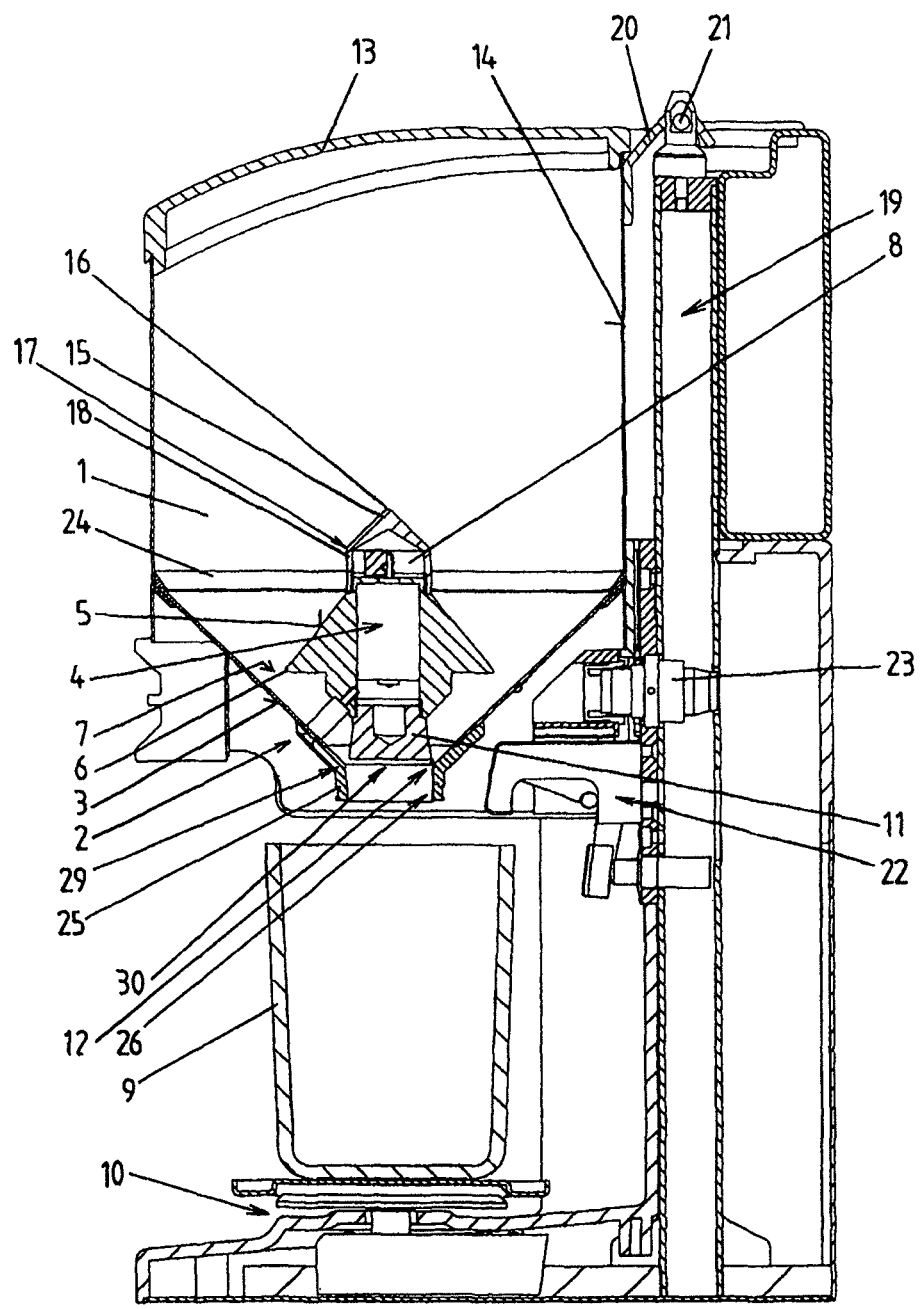
FIG. 1 shows a first embodiment of a metering device according to the invention in its entirety in a vertical section.

The metering device according to the invention for powdery substances involves, in particular, the preparation of dental and dentistry-related powder compounds. Such powder compounds are needed in dosed quantities of a maximum of 2000 grams, with typical required quantities lying at 50 to 500 grams. In addition, for dental and dentistry-related powder compounds, a large metering accuracy must be able to be maintained. Thus, a metering accuracy of ±0.5 grams should be achieved. For the variants shown in FIG. 1, the powder compounds can be filled in a storage container 1 and a discharge device 2 is allocated to this storage container 1. The lower region 3 of the storage container 1 has a construction that tapers, advantageously downward, in the shape of a cone or pyramid or in some other way. In the storage container 1, there is an insert 4 that has at least one section 5 with a construction that tapers upward advantageously in the shape of a cone or pyramid or in some other way, with this section being arranged in the tapered, lower region 3 of the storage container 1. In this embodiment, an essentially ring-shaped passage opening 7 remains free between the lower edge 6 of the tapering section 5 of the insert 2 and the tapered, lower region 3 of the storage container 1. The insert 2 has a vibration device 8.

In the construction variant shown in FIG. 1, a vessel 9 holding the dosed powder can be set on a weighing device 10. The weighing device 10 and the vibration device 8 are in active connection with each other.

The metering can be implemented in the construction according to the invention by means of a corresponding vibration device. This vibration device 8 can be integrated into the insert 4 and/or can be allocated to the storage container 1. In the storage container 1, an arrangement of the vibration device both on the inside and also on the outside is conceivable.

For the operation of this metering device, a special method is used. The vibration device 8 is operated at the beginning and at the end of the metering process with a smaller vibration frequency than in an intermediate phase of the metering process. The weighing device 10 here sets the control of the vibration period. Thus, if needed, it can be set exactly how much quantity of the powder mass should be filled from the storage container 1 into the vessel 9. This provides an additional possibility for improving the exact final delivery, that is, the concluding fine metering. This method sequence then provides that the vibration device 8 is completely turned off in a way that can be preset before reaching the desired delivery quantity and the vibration device 8 is then switched to a maximum value of the vibration frequency for the fine metering and the vibration frequency is reduced from this setting continuously or in steps up to a minimum value, advantageously zero.

The vibration frequency can be set or preset in steps or continuously for adapting to different types of powder compounds.

A passage opening 7 that has an advantageously closed-periphery, ring-shaped construction has been discussed above. However, in the scope of the invention it is also possible that several bores or through holes or sieve-like sections are provided as passage openings. The optimal solution can be used according to the construction and special application of the metering device.

On the bottom side of the insert 4, a pin 11 or a sleeve projects downward, reducing the through-flow cross section. The pin 11 or the sleeve that projects from the bottom side of the insert 4 is advantageously held so that it can be replaced.

The passage opening(s) 7 remaining between the tapered, lower region 3 of the storage container 1 and the lower edge 6 of the tapering section 5 of the insert 4 are larger in cross section than the ring-shaped passage opening 12 remaining between the tapered, lower region of the storage container 1 and the pin 11 or the sleeve.

The insert 4 is supported so that it is fixed in position relative to the tapered, lower region 3 of the storage container 1. This support can be realized, for example, by a tubular part by means of which the electrical line can also be guided to the vibration device. Additional support can be arranged offset by 120°, for example, also only in the form of rubber buffers.

However, it is also conceivable to connect the insert 4 rigidly, that is, without rubber buffers, to storage container 1. Then there is also the possibility to accommodate the vibration device 8 in the insert 4, wherein then the storage container 1 is exposed like the insert itself to corresponding vibrations.

In one special embodiment, a refill inspection arrangement that can be detected optically and/or acoustically can be arranged on a cover 13 or a wall 14 of the storage container 1.

The insert 4 has a conical or pyramidal section 15 lying above the tapering section 5, wherein the tip 16 of this conical or pyramidal section points upward and its lower edge 17 has a smaller diameter than the lower edge 6 of the tapering section 5 and is connected to the tapering section 5 by a cylindrical transition section 18. The vibration device 8 could be housed in this transition section 18.

In a special variant likewise shown in FIG. 1, however, the storage container 1 is held so that it can be removed and locked together with the insert 4 on a base frame 19. Here, one possible construction provides a hook-like closure 20 on the upper end of the storage container 1, wherein, by use of this closure, the storage container 1 can be suspended on a support pin 21 on the base frame 19. Preferably, the storage container 1 is held so that it can be locked in the suspended position with locking elements 22 arranged on the lower end region.

In this context, it is advantageous to provide plug devices 23 in the region of the locking elements 22 between storage container 1 and base frame 19 for the electrical connection for the operation, for example, of the vibration device 8.

Especially when no or only very little vibration should be felt on the storage container, advantageously strip-like intermediate layers made from a vibration-blocking material are arranged between the storage container 1 and the base frame 19.

In the scope of the invention, however, a construction is also possible, in principle, in which the storage container is connected rigidly to the base frame. In most cases, the powder compounds are already on the market in small packages, so that these can be emptied into the base container on the spot, without generating too much dust.

From FIG. 1 it is further visible that the essentially cylindrical storage container 1 and the tapered, lower region 3 are formed from two sections separated from each other. On the upper peripheral edge of the tapered region 3 there is a periphery-closed sealing element 24, so that no powder compounds can penetrate to the outside between these parts.

In the embodiment according to FIG. 1, an outlet element 25 through which the powdery substance to be dosed flows from the storage container 1 into the vessel 9 is arranged on the lower outlet opening 29 of the storage container 1 or its lower region 3. In the first embodiment, an essentially smooth inner wall section 26 comprises the through-flow opening 30 of the outlet element 25. This arrangement functions without a problem as long as no substances are to be dosed that become electro-statically charged while or before flowing through the outlet element. In contrast, if substances, such as, e.g., cement, which tend to become electro-statically charged are to be dosed, then this could disturb the metering process, in that the particles to be dosed then no longer flow in a uniform jet, but instead spray outward uncontrollably due to their electrostatic charging from the outlet element 25 or from its through-flow opening 30. Conventional methods for reducing the electrical charging of the dosed powder particles consist in the use of metallic wires or screens at which the charge should be removed from the charged powder particles during the metering or blowing. According to experience, however, this does not lead to the desired result to a sufficient degree.

FIGS. 2 and 3 now show a variant of the invention modified in the region of the outlet element 25, wherein the advantage in this variant consists in that the powder particles do not become electrically charged at all during the metering. FIG. 3 shows the detail A from FIG. 2 enlarged. Up to the differences to be discussed now in the following, the second embodiment according to FIGS. 2 and 3 is constructed analogous to the first embodiment according to FIG. 1, so that, in this respect, the above statements can be referenced.

The difference with the first embodiment according to FIG. 1 lies in the construction of the outlet element 25 or, in particular, its inner wall section 26. In the second embodiment according to FIGS. 2 and 3 it is provided that the lower region 3 of the storage container 1 has the outlet opening 29 for the powdery substances, wherein an outlet element 25 is arranged on the outlet opening 29, with this outlet element having at least one inner-wall section 29 comprising a through-flow opening 30 that tapers in cross section downward for the powdery substances, wherein the inner-wall section 29 has, looking down from above, a sequence of alternating recessed regions 27 and projecting regions 28. In this way, a shape of the inner-wall section 29 extending, in particular, at an angle to the vertical is realized that has recesses in the form of the recessed regions 27 arranged alternating with the projecting regions 28. Powdery substances can collect in the recesses constructed by the recessed regions 27. If the recessed regions 27 are filled with powder, then the subsequently trickling powdery substance predominantly flows over the powdery material collected in the recesses or recessed regions 27, wherein an electrostatic charging of the subsequently trickling powdery substance and thus the problem mentioned above are avoided. In this way it is achieved that the subsequently trickling material can be dosed in the form of a uniform jet and disruptions no longer occur due to electrostatic charging. So that the collection of powdery substance in the recessed regions 27 covers the entire inner-wall section 29 as much as possible, it is preferably provided that the projections regions 28 have a sharp-edged construction. In principle, the recesses or recessed regions and the projecting regions 28 arranged alternating with these recessed regions have or form different tub-shaped constructions or the like. In one preferred embodiment, as is to be seen, in particular, in FIG. 3, the inner-wall section 29 has a stairs-like or step-like construction for forming the recessed regions 27 and the projecting regions 28.

The outlet elements 25 both of the first embodiment and also of the second embodiment could be made from different materials. Preferred configurations provide that these are metal bodies. The outlet elements 25 could be constructed as an interchangeable ring that can be screwed on or plugged in and held in a corresponding mounting on the storage container 1 or its outlet opening 29.

In the present invention, the supply of a fluid is also definitely possible, so that, in addition to the powder mass, an exactly adapted quantity of fluid can also be delivered. The supply of the fluid, however, is not realized by means of the storage container, but instead by means of a separate supply line. It would be definitely conceivable to also use the invention when different powder compounds are to be combined into one mixture. Then, for example, several storage containers could be provided with separate vibration devices that possibly lead the dosed powder compounds into the same vessel and to the one weighing device.

LEGEND TO THE REFERENCE SYMBOLS

1 Storage container
2 Discharge device
3 Region
4 Insert
5 Section
6 Edge
7 Passage opening
8 Vibration device
9 Vessel
10 Weighing device
11 Pin
12 Passage opening
13 Cover
14 Wall
15 Conical or pyramidal section
16 Tip
17 Edge
18 Transition section
19 Base frame
20 Closure
21 Support pin
22 Locking elements
23 Plug devices
24 Sealing element
25 Outlet element
26 Inner wall section
27 Recessed region
28 Projecting region
29 Outlet opening
30 Through-flow opening

The invention claimed is:

1. Metering device for powdery substances, comprising a storage container (1) and a discharge device (2) allocated to the storage container (1), a lower region (3) of the storage container (1) has a tapered construction and an insert (4) that has at least one section (5) tapering upward is arranged in the storage container (1), the at least one section that tapers upward is arranged in the tapered, lower region (3) of the storage container (1), at least one passage opening (7) remains free between a lower edge (6) of the tapering section (5) of the insert (4) and the tapered, lower region (3) of the storage container (1) and a vibration device (8) is allocated to at least one of the insert (4) or the storage container (1), wherein a lower region (13) of the storage container (1) has an outlet opening (29) for the powdery substance, an outlet element (25) is arranged at the outlet opening (29) and the outlet element (25) has at least one inner-wall section comprising a through-flow opening (30) that tapers in cross section downward, and the inner-wall section (29) has, looking down from above, a sequence of alternating recesses (27) and projecting regions (28) following one after the other.

2. Metering device according to claim 1, wherein a vessel (9) adapted to hold dosed powder is placed on a weighing device (10) of the metering device, and the weighing device (10) and the vibration device (8) are in active connection with each other.

3. Metering device according to claim 1, wherein the lower region (3) of the storage container (1) has a construction tapered in a cone or pyramid shape.

4. Metering device according to claim 1, wherein the at least one passage opening (7) has a closed-periphery, ring-shaped construction or includes several bores or through holes or screen-like sections.

5. Metering device according to claim 1, wherein a pin (11) or a sleeve that reduces a through-flow cross section projects downward from a bottom side of the insert (4).

6. Metering device according to claim 5, wherein the at least one passage opening (7) remaining between the tapered lower region (3) of the storage container (1) and the lower edge (6) of the section (5) of the insert (4) tapering upward is larger in cross section than a ring-shaped passage opening (12) remaining between the tapered lower region (3) of the storage container (1) and the pin (11) or the sleeve.

7. Metering device according to claim 1, wherein the insert (4) is supported so that it is fixed in position relative to the tapered lower region (3) of the storage container (1).

8. Metering device according to claim 1, wherein the insert (4) has a conical or pyramidal section (15) lying above the tapering section (5), the tip (16) of the conical or pyramidal section points upward and a lower edge (17) thereof has a smaller diameter than the lower edge (6) of the tapering section (5) and is connected to the tapering section (5) by a cylindrical transition section (18).

9. Metering device according to claim 1, wherein the storage container (1) is held so that it can be removed from or locked together with the insert (4) on a base frame (19), and the storage container (1) is suspendable by a hook-like upper closure (20) on a support pin (21) on the base frame (19) and is held so that the storage container (1) can be locked in a suspended position with locking elements (22) arranged on the lower end region.

10. Metering device according to claim 9, wherein in a region of the locking elements (22), plug devices (23) for electrical connection for the operation of the vibration device (8) are provided between storage container (1) and base frame (19).

11. Metering device according to claim 1, wherein the projecting regions (28) are sharp edged.

12. Metering device according to claim 1, wherein the inner-wall section (29) has a stairs-like or step-like construction.

13. Method for the operation of a metering device according to claim 1, wherein the vibration device (8) is operated at a beginning and at an end of a metering process with a smaller vibration frequency than in an intermediate phase of the metering process.

14. Method according to claim 13, wherein control of a vibration period is set by a weighing device (10) in active connection with the vibration device (8).

15. Method according to claim 14, wherein the vibration device (8) is completely turned off in a way that can be preset before reaching a desired delivery quantity and then, for fine metering, the vibration device (8) is switched to a maximum value of the vibration frequency and the vibration frequency is reduced from the maximum value setting continuously or in steps to a minimal value.

16. Method according to claim 15, wherein the minimal valve is zero.

17. Metering device according to claim 5, wherein the pin (11) or the sleeve is replaceably connected to the bottom side of the insert (4).

18. Metering device according to claim 1, wherein the insert (4) is rigidly connected to the storage container (1) and the vibration device is arranged in the insert (4).

19. Metering device according to claim 3, wherein the at least one section (5) of the insert (4) that tapers upward tapers upwardly in s conical or pyramidal shape.

\* \* \* \* \*